US006794649B2

(12) United States Patent
Thrash et al.

(10) Patent No.: US 6,794,649 B2
(45) Date of Patent: Sep. 21, 2004

(54) SPECTROPHOTOMETRIC DETERMINATION OF GAS PHASE COMPOSITIONS

(75) Inventors: Robert J. Thrash, St. Charles, IL (US); Thomas F. Cullen, Des Plaines, IL (US); Davoud Khorzad, Lake Forest, IL (US); Jimmy Fisher, Hawthorn Woods, IL (US)

(73) Assignee: Pharmaceutical Systems, Inc., Mundelein, IL (US)

( * ) Notice: Subject to any disclaimer, the term of this patent is extended or adjusted under 35 U.S.C. 154(b) by 397 days.

(21) Appl. No.: 09/901,221

(22) Filed: Jul. 9, 2001

(65) Prior Publication Data

US 2003/0006375 A1 Jan. 9, 2003

(51) Int. Cl.[7] .............................. A61L 2/08; G01N 21/00
(52) U.S. Cl. .............................. 250/339.13; 250/339.12
(58) Field of Search ........................ 250/339.13, 339.12, 250/339.06, 339.01, 338.1, 336.1

(56) References Cited

U.S. PATENT DOCUMENTS

| | | |
|---|---|---|
| 4,314,344 A | 2/1982 | Johns et al. |
| 4,427,772 A | 1/1984 | Kodera et al. |
| 4,525,265 A | 6/1985 | Abe et al. |
| 4,795,707 A | 1/1989 | Niiyama et al. |
| 4,843,867 A | 7/1989 | Cummings |
| 5,007,232 A | 4/1991 | Caudill |
| 5,097,130 A | 3/1992 | Koashi et al. |
| 5,139,957 A | 8/1992 | Grack |
| 5,167,927 A | 12/1992 | Karlson |
| 5,474,908 A | 12/1995 | Kurono et al. |
| 5,482,684 A | 1/1996 | Martens et al. |
| 5,516,489 A | 5/1996 | Melgaard et al. |
| 5,518,591 A | 5/1996 | Pulliainen et al. |
| 5,600,142 A | 2/1997 | Van Den Berg et al. |
| 5,608,156 A | 3/1997 | Ando et al. |
| 5,620,656 A | 4/1997 | Wensky et al. |
| 5,788,925 A | 8/1998 | Pai et al. |
| 5,789,175 A | 8/1998 | Priest |
| 5,847,392 A | 12/1998 | Van Den Berg et al. |
| 5,847,393 A | 12/1998 | Van Den Berg et al. |
| 5,872,359 A | 2/1999 | Stewart et al. |
| 5,892,229 A | 4/1999 | Crozier et al. |
| 5,938,917 A | 8/1999 | Mulchandani |
| 5,942,754 A | 8/1999 | Yamaguchi et al. |
| 5,972,199 A | 10/1999 | Heller et al. |
| 6,075,246 A | 6/2000 | Stock |
| 6,156,267 A | 12/2000 | Pai et al. |
| 6,189,368 B1 | 2/2001 | Ichida et al. |
| 2003/0012689 A1 * | 1/2003 | Caputo .................. 422/32 |

FOREIGN PATENT DOCUMENTS

| | | |
|---|---|---|
| GB | 1016421 | 7/2000 |
| JP | 2-276950 | 11/1990 |

* cited by examiner

*Primary Examiner*—David Porta
*Assistant Examiner*—Christine Sung
(74) *Attorney, Agent, or Firm*—Stephen P. Gilbert; Bryan Cave LLP

(57) ABSTRACT

Methods are disclosed for determining the monotonic functional relationship between (A) the integrated absorbance of spectral energy within a spectral region of interest of an analyte (i) that decomposes during the time experimental spectral data for determining the relationship are being obtained, or (ii) whose spectral data are pressure sensitive at pressures below a given pressure, or (iii) that decomposes during the time the spectral data are being obtained and whose spectral data are pressure sensitive and (B) the concentration of the analyte before decomposition commences. Methods are also disclosed for using the monotonic functional relationship to determine the concentration of the analyte in an unknown from the integrated absorbance of spectral energy within the spectral region of interest for the unknown. The methods are useful for determining the concentration of gaseous analytes, such as hydrogen peroxide, whose concentrations must be accurately and rapidly determined in processes such as sterilization processes at the time the processes are being conducted.

82 Claims, 5 Drawing Sheets

| Prepared Conc. (mg/L) | Time Zero Abs. | Regressed Conc. (mg/L) | %Error |
|---|---|---|---|
| 0.206 | 1.425 | 0.211 | 2.2% |
| 0.217 | 1.310 | 0.187 | -13.9% |
| 0.366 | 1.941 | 0.320 | -12.7% |
| 0.436 | 2.275 | 0.390 | -10.6% |
| 0.883 | 4.789 | 0.921 | 4.3% |
| 1.008 | 5.229 | 1.014 | 0.6% |
| 1.135 | 6.086 | 1.194 | 5.3% |
| 1.793 | 8.992 | 1.808 | 0.8% |
| 1.856 | 9.571 | 1.930 | 4.0% |
| 2.406 | 12.726 | 2.596 | 7.9% |
| 2.540 | 11.955 | 2.433 | -4.2% |
| 2.893 | 13.042 | 2.663 | -8.0% |
| 3.437 | 17.060 | 3.511 | 2.1% |
| slope | 4.738 | | |
| intercept | 0.426 | | |
| correlation | 0.996 | | |
| %RSD | 6.7% | | |

Fig. 5

SPECTROPHOTOMETRIC DETERMINATION OF GAS PHASE COMPOSITIONS

BACKGROUND OF THE INVENTION

1. Technical Field

This invention concerns the field of spectroscopy and, more specifically, the use of spectrophotometry to determine gas phase concentrations.

2. Background Art

There are many methods used to detect and/or determine the concentration of an analyte in a mixture or solution. See, for example, U.S. Pat. Nos. 4,314,344, 4,427,772, 4,525,265, 4,795,707, 4,843,867, 5,139,957, 5,167,927, 5,474,908, 5,482,684, 5,516,489, 5,518,591, 5,600,142, 5,608,156, 5,788,925, 5,789,175, 5,847,392, 5,847,393, 5,872,359, 5,892,229, 5,938,917, 5,942,754, 5,972,199, 6,075,246, 6,156,267, and 6,189,368; and European Patent Application No. EP 1,016,421. (All of the foregoing documents, as well as all other documents cited or otherwise referenced herein, are incorporated herein in their entireties for all purposes.)

Some of those documents concern detecting and/or determining the concentration of a species in gas, vapor, or plasma. See, e.g., U.S. Pat. Nos. 4,314,344, 4,843,867, 5,139,957, 5,167,927, 5,482,684, 5,516,489, 5,600,142, 5,608,156, 5,788,925, 5,789,175, 5,847,392, 5,847,393, 5,872,359, 5,892,229, 6,075,246, 6,156,267, 6,189,368; and European Patent Application No. EP 1,016,421.

Some of those documents concern detecting and/or determining the concentration of hydrogen peroxide. See, e.g., U.S. Pat. Nos. 4,427,772, 4,525,265, 4,795,707, 4,843,867, 5,139,957, 5,167,927, 5,474,908, 5,516,489, 5,518,591, 5,600,142, 5,608,156, 5,788,925, 5,789,175, 5,847,392, 5,847,393, 5,872,359, 5,892,229, 5,938,917, 5,942,754, 5,972,199, 6,156,267, 6,189,368; and European Patent Application No. EP 1,016,421.

Some of those documents concern detecting and/or determining the concentration of hydrogen peroxide using spectrophotometry, e.g., using infrared or near-infrared energy. See, e.g., U.S. Pat. Nos. 5,600,142, 5,847,392, 5,847,393, 5,872,359, 5,892,229, 5,942,754; and European Patent Application No. EP 1,016,421.

It is known to determine successive values of a parameter for analytes that decompose after the decomposition has begun and to extrapolate from those successive values back to time zero (the moment just before decomposition begins) to estimate the value of the parameter at time zero. To applicants' knowledge, such a method has not been used for peracids or peroxides (e.g., hydrogen peroxide).

Hydrogen peroxide is used in connection with bleaching, sterilization, and other processes, and there is a need to be able to measure or determine its concentration accurately. In particular, for vapor phase sterilization, the concentration of hydrogen peroxide in the gas phase must be accurately known; however, development of a method for accurately determining the concentration of hydrogen peroxide in the gas phase is hampered by the fact that hydrogen peroxide decomposes in the gas phase. Hydrogen peroxide decomposition increases with increasing temperature (at room temperature, an increase of 10° C. is believed to more than double the rate of decomposition), with increasing pH (especially in the alkaline range), with increasing contamination (e.g., with transition metals), and with exposure to light (particularly ultraviolet light).

Hydrogen peroxide is typically sold in aqueous solution, for example, at concentrations of 3% w/w, 10% w/w, 30% w/w, 35% w/w, and higher (e.g., 70% w/w), and the manufacturers generally add proprietary stabilizers (e.g., chelants/sequestrants such as organic and inorganic phosphates and/or stannates and/or silicates) to the liquid solution to minimize decomposition. Unfortunately, these stabilizers do not function in the vapor phase and once an aqueous liquid solution of hydrogen peroxide is vaporized, as it typically is in hydrogen peroxide vapor phase sterilization processes, decomposition of the hydrogen peroxide immediately begins and continues unabated.

Continuous decomposition of hydrogen peroxide in the vapor phase makes it all the more difficult to determine a relationship between the concentration of the hydrogen peroxide in the vapor phase and a physical property of the hydrogen peroxide that can be measured rapidly (e.g., absorbance of spectral energy within a preselected spectral region characteristic of the hydrogen peroxide) and which relationship can therefore be used to monitor the hydrogen peroxide concentration (e.g., during a hydrogen peroxide sterilization process). This is because such a relationship must be established experimentally and doing so requires, among other things, collecting a sufficient number of replicate data points in real time, but that unfortunately is while the hydrogen peroxide itself is continuing to decompose. In other words, while the physical property indicative of the concentration of hydrogen peroxide is being measured repeatedly so that the relationship between concentration and the physical property can be established, the hydrogen peroxide concentration is decreasing and the measured value of the physical property is changing.

Despite all the attempts that have been made, the need still remains for a rapid and accurate method for determining hydrogen peroxide concentration in the vapor phase. More generally, the need still exists for a rapid and accurate method for determining the concentration of an analyte that decomposes.

SUMMARY OF THE INVENTION

A rapid and accurate method for determining hydrogen peroxide concentration in the vapor phase has now been developed. More generally, a rapid and accurate method for determining the concentration of an analyte that decomposes and/or whose spectral data are "pressure sensitive" (as defined herein) has now been developed. As explained below, applicants discovered that hydrogen peroxide not only decomposes but that its spectral data are pressure sensitive.

Thus, for hydrogen peroxide, the method of determining the concentration makes use of a monotonic functional relationship between the concentration of hydrogen peroxide in the vapor phase and the total (integrated) absorbance of spectral energy within a preselected spectral region characteristic of hydrogen peroxide, preferably the spectral region of wavenumbers 1180 cm$^{-1}$ (approximately 8475 nanometers) through 1331 cm$^{-1}$ (approximately 7513 nanometers). Thus, a first part of the invention concerns a method for using the relationship to determine (or estimate or predict) from the integrated absorbance of spectral energy for an unknown (i.e., unknown sample) what the concentration of hydrogen peroxide (or other analyte) is in that unknown. A second part of the invention concerns a method for establishing or determining the monotonic functional relationship for hydrogen peroxide (or other analyte).

In connection with the development of the second part of the invention as it applies to hydrogen peroxide, applicants made the surprising discovery that at pressures below about 230 torr (approximately 30.7 kPa), the integrated absorbance for hydrogen peroxide is about 20% lower than it would otherwise be if the pressure were above the pressure at which this phenomenon occurs or at least becomes noticeable (i.e., above about 230 torr). The significance of this is that use of data subject to this phenomenon (i.e., integrated absorbance data that are significantly lower than they would otherwise be) to establish the monotonic functional relationship will result in erroneous predicted hydrogen peroxide concentrations in some cases. Applicants do not know why this phenomenon of significantly lower integrated absorbance occurs.

As indicated herein, if it is desired to estimate, the vapor phase hydrogen peroxide concentration in an unknown, the integrated absorbance for the unknown over the spectral region of interest is determined and the previously established monotonic functional relationship between concentration and integrated absorbance is used. That relationship is typically established from absorbance data for different known hydrogen peroxide concentrations. Applicants discovered that, most surprisingly, for a constant amount of hydrogen peroxide in a chamber (and therefore for which the integrated absorbance within the spectral region of interest was expected to remain constant), when increasing amounts of dry air (which is essentially inert to the hydrogen peroxide) were added to the chamber, thereby raising the total pressure, the integrated absorbance in fact varied: it was approximately constant at total pressures from about 230 torr up to atmospheric pressure but was approximately 20% lower at total pressures below that point.

Accordingly, if the relationship between hydrogen peroxide concentration and integrated absorbance must be known for a constant pressure (e.g., atmospheric pressure) because, for example, the relationship will be used to predict hydrogen peroxide concentration in a system operating at that pressure (e.g., atmospheric pressure), the data used to establish the relationship cannot be generated at a pressure that is too low. If too low a pressure is used for obtaining some or all of the data from which the relationship between integrated absorbance and concentration will be established, the relationship determined from that data will not accurately reflect the relationship at the higher system operating pressure throughout at least some or all of the concentration range. As a result, an integrated absorbance measured at the higher system operating pressure that falls within the "erroneous" part of the monotonic functional relationship determined using the "low" integrated absorbance values will predict too high a concentration (i.e., will indicate a concentration in the system higher than is actually present). Such over-prediction of the concentration cannot be tolerated in any application in which the hydrogen peroxide concentration must be accurately known (e.g., hydrogen peroxide sterilization systems).

As will be explained in more detail below, applicants solved this problem in the following manner. While obtaining the data for establishing the hydrogen peroxide concentration-absorbance relationship, they intentionally rapidly added to the hydrogen peroxide aliquots of known concentration a sufficient amount of a gas essentially inert (i.e., chemically, spectrally, etc.) to the hydrogen peroxide (namely, dry air) to bring the total pressure above the pressure P at which the "low" integrated absorbance values would otherwise have been obtained so that the data were all obtained at pressures above pressure P.

Thus, in a first aspect, the invention concerns a method for determining the monotonic functional relationship between (A) the integrated absorbance of spectral energy within a spectral region of interest of an analyte that decomposes during the time experimental spectral data for determining the relationship are being obtained and whose spectral data are pressure sensitive below a total pressure P and (B) the concentration of the analyte before decomposition commences, knowledge of the monotonic functional relationship being useful for determining the concentration of the analyte in an unknown that is at a total pressure not less than pressure P from the integrated absorbance of spectral energy within the spectral region of interest for the unknown, the method comprising the steps:

(a) for a first known initial concentration of the analyte and while intentionally maintaining the total pressure at a pressure not less than pressure P because of the spectral data being pressure sensitive below pressure P: (i) determining the integrated absorbance of spectral energy within the spectral region of interest at a first time after the commencement of the obtention of spectral data, (ii) determining the integrated absorbance of spectral energy within the spectral region of interest at one or more times subsequent to the first time and different from each other if more than one subsequent time is used, and (iii) extrapolating from the integrated absorbance for the first time and the one or more subsequent times to the time at which the decomposition of the analyte commences to thereby establish at a time before the decomposition commences an estimated integrated absorbance of spectral energy within the spectral region of interest for the first known initial concentration;

(b) for each of one or more additional known initial concentrations of the analyte different from the first known concentration and different from each other if more than one additional initial concentration is used and while intentionally maintaining the total pressure at a pressure not less than pressure P because of the spectral data being pressure sensitive below pressure P: (i) determining the integrated absorbance of spectral energy within the spectral region of interest at a first time after the commencement of the obtention of spectral data, (ii) determining the integrated absorbance of spectral energy within the spectral region of interest at one or more times subsequent to the first time and different from each other if more than one subsequent time is used, and (iii) extrapolating from the integrated absorbance for the first time and the one or more subsequent times to the time at which the decomposition of the analyte commences to thereby establish at a time before the decomposition commences an estimated integrated absorbance of spectral energy within the spectral region of interest for each of the one or more additional known initial concentrations; and (c) associating each of the known initial concentrations with its respective estimated integrated absorbance of spectral energy within the spectral region of interest to thereby determine for the analyte at a total pressure not less than pressure P the monotonic functional relationship between the concentration before the decomposition commences and the integrated absorbance of spectral energy within the spectral region of interest of the analyte.

In a second aspect, the invention concerns a method for determining in an unknown the concentration of an analyte that decomposes and whose spectral data are pressure sensitive below a total pressure P, the method comprising the steps: (d) while intentionally maintaining the total pressure at a pressure not less than pressure P because of the spectral data being pressure sensitive below pressure P, carrying out the method of the first aspect of this invention to determine the monotonic functional relationship for the analyte, (e) while intentionally maintaining the total pressure at a pressure not less than pressure P because of the spectral data being pressure sensitive below pressure P, determining the integrated absorbance for the unknown within the spectral region of interest, and (f) from the monotonic functional relationship determined in step (d) and the integrated absorbance determined in step (e), determining the concentration of the analyte in the unknown.

In a third aspect, the invention concerns a method for determining in an unknown the concentration of an analyte that decomposes and whose spectral data are pressure sensitive below a total pressure P, a monotonic functional relationship between the concentration of the analyte and integrated absorbance at a total pressure not less than pressure P having been previously established using the method of the first aspect of this invention, the method comprising the steps: (a) while intentionally: maintaining the total pressure at a pressure not less than pressure P because of the spectral data being pressure sensitive below pressure P, determining the integrated absorbance for the unknown within the spectral region of interest and (b) from the monotonic functional relationship previously determined at a total pressure not less than pressure P using the method of the first aspect of this invention and the integrated absorbance determined in step (a), determining the concentration of the analyte in the unknown.

In a fourth aspect, the invention concerns a method for determining the monotonic functional relationship between (A) the integrated absorbance of spectral energy within a spectral region of interest of an analyte that is a peracid or a peroxide and that decomposes during the time experimental spectral data for determining the relationship are being obtained and (B) the concentration of the analyte before decomposition commences, knowledge of the monotonic functional relationship being useful for determining the concentration of the analyte in an unknown from the integrated absorbance of spectral energy within the spectral region of interest for the unknown, the method comprising the steps:

(a) for a first known initial concentration of the analyte: (i) determining the integrated absorbance of spectral energy within the spectral region of interest at a first time after the commencement of the obtention of spectral data, (ii) determining the integrated absorbance of spectral energy within the spectral region of interest at one or more times subsequent to the first time and different from each other if more than one subsequent time is used, and (iii) extrapolating from the integrated absorbance for the first time and the one or more subsequent times to the time at which the decomposition of the analyte commences to thereby establish at a time before the decomposition commences an estimated integrated absorbance of spectral energy within the spectral region of interest for the first known initial concentration;

(b) for each of one or more additional known initial concentrations of the analyte different from the first known concentration and different from each other if more than one additional initial concentration is used: (i) determining the integrated absorbance of spectral energy within the spectral region of interest at a first time after the commencement of the obtention of spectral data, (ii) determining the integrated absorbance of spectral energy within the spectral region of interest at one or more times subsequent to the first time and different from each other if more than one subsequent time is used, and (iii) extrapolating from the integrated absorbance for the first time and the one or more subsequent times to the time at which the decomposition of the analyte commences to thereby establish at a time before the decomposition commences an estimated integrated absorbance of spectral energy within the spectral region of interest for each of the one or more additional known initial concentrations; and (c) associating each of the known initial concentrations with its respective estimated integrated absorbance of spectral energy within the spectral region of interest to thereby determine for the analyte the monotonic functional relationship between the concentration before the decomposition commences and the integrated absorbance of spectral energy within the spectral region of interest of the analyte.

In a fifth aspect, the invention concerns a method for determining in an unknown the concentration of an analyte that is a peracid or a peroxide and that decomposes, the method comprising the steps: (d) carrying out the method of the fourth aspect of the invention to determine the monotonic functional relationship for the analyte, (e) determining the integrated absorbance for the unknown within the spectral region of interest, and (f) from the monotonic functional relationship determined in step (d) and the integrated absorbance determined in step (e), determining the concentration of the analyte in the unknown.

In a sixth aspect, the invention concerns a method for determining in an unknown the concentration of an analyte that is a peracid or a peroxide and that decomposes, a monotonic functional relationship between the concentration of the analyte and integrated absorbance having been previously established using the method of the fourth aspect of the invention, the method comprising the steps: (a) determining the integrated absorbance for the unknown within the spectral region of interest and (b) from the monotonic functional relationship previously determined using the method of the fourth aspect of the invention and the integrated absorbance determined in step (a), determining the concentration of the analyte in the unknown.

In a seventh aspect, the invention concerns a method for determining the monotonic functional relationship between (A) the integrated absorbance of spectral energy within a spectral region of interest of an analyte in the gas phase whose spectral data are pressure sensitive below total pressure P and (B) the concentration of the analyte, knowledge of the monotonic functional relationship being useful for determining the concentration of the analyte in a gas phase unknown that is at a total pressure not less than pressure P from the integrated absorbance of spectral energy within the spectral region of interest for the unknown, the method comprising the steps:

(a) for a first known initial concentration of the analyte and while intentionally maintaining the total pressure at a pressure not less than pressure P because of the spectral data being pressure sensitive below pressure P, determining the integrated absorbance of spectral energy within the spectral region of interest for the first known initial concentration;

(b) for each of one or more additional known initial concentrations of the analyte different from the first known concentration and different from each other if more than one additional initial concentration is used and while intentionally maintaining the total pressure at a pressure not less than pressure P because of the spectral data being pressure sensitive below pressure P, determining the integrated absorbance of spectral energy within the spectral region of interest for each of the one or more additional known initial concentrations; and (c) associating each of the known initial concentrations with its respective integrated absorbance of spectral energy within the spectral region of interest to thereby determine for the analyte at a total pressure not less than pressure P the monotonic functional relationship between the concentration and the integrated absorbance of spectral energy within the spectral region of interest of the analyte.

In an eighth aspect, the invention concerns a method for determining in a gas phase unknown the concentration of an analyte whose spectral data are pressure sensitive below a total pressure P, the method comprising the steps: (d) while intentionally maintaining the total pressure at a pressure not less than pressure P because of the spectral data being pressure sensitive below pressure P, carrying out the method of the seventh aspect of the invention to determine the monotonic functional relationship for the analyte, (e) while intentionally maintaining the total pressure at a pressure not less than pressure P because of the spectral data being pressure sensitive below pressure P, determining the integrated absorbance for the unknown within the spectral region of interest, and (f) from the monotonic functional relationship determined in step (d) and the integrated absorbance determined in step (e), determining the concentration of the analyte in the unknown.

In a ninth aspect, the invention concerns a method for determining in an unknown the concentration of an analyte whose spectral-data are pressure sensitive below a total pressure P, a monotonic functional relationship between the concentration of the analyte and integrated absorbance having been previously established using the method of the seventh aspect of the invention, the method comprising the steps: (a) while intentionally maintaining the total pressure at a pressure not less than pressure P because of the spectral data being pressure sensitive below pressure P, determining the integrated absorbance for the unknown within the spectral region of interest and (b) from the monotonic functional relationship previously determined using the method of the seventh aspect of the invention and the integrated absorbance determined in step (a), determining the concentration of the analyte in the unknown.

In preferred embodiments of the methods of the invention: pressure P is determined prior to carrying out the other steps of one or more of the methods; and/or the total pressure is maintained in each of the steps of one or more of the methods at not less than pressure P by adding to the analyte as needed to raise the pressure a gas that is inert to the analyte; and/or the gas that is inert to the analyte is dry air; and/or the analyte is a sterilant; and/or the analyte is a volatile inorganic or organic peroxidant; and/or the analyte is a peracid or a peroxide; and/or the analyte is a peracid; and/or the analyte is a peroxide; and/or the analyte is hydrogen peroxide; and/or the spectral region of interest is the infrared region; and/or the spectral region of interest is from about 1180 $cm^{-1}$ to about 1331 $cm^{-1}$.

This invention provides a rapid and accurate method for determining hydrogen peroxide concentration, as well the concentration of other analytes and particularly in the vapor phase. This invention has still other features and benefits that will be apparent to one skilled in the art.

BRIEF DESCRIPTION OF THE DRAWINGS

To facilitate further description of the invention, the following drawings are provided in which:

FIG. 5 is a table showing, in the first column, actual (prepared) hydrogen peroxide concentrations at the time of injection of the aqueous hydrogen peroxide liquid solution into the chamber; in the second column, for each actual concentration the integrated absorbance determined using a method of this invention for "time zero" ("time zero" or to is the time of injection of aqueous hydrogen peroxide solution into the chamber, at which time all of the hydrogen peroxide and water in the liquid solution rapidly flash into the gas phase and decomposition of the hydrogen peroxide commences); in the third column, the "regressed concentration" (i.e., the time zero hydrogen peroxide concentration determined using the monotonic functional relationship established through a method of this invention and shown in FIG. 4); and, in the fourth column, the percentage error in the hydrogen peroxide concentration predicted by the monotonic functional relationship as compared to the actual hydrogen peroxide concentration (calculated as regressed concentration minus actual concentration divided by actual concentration).

Figure 1:
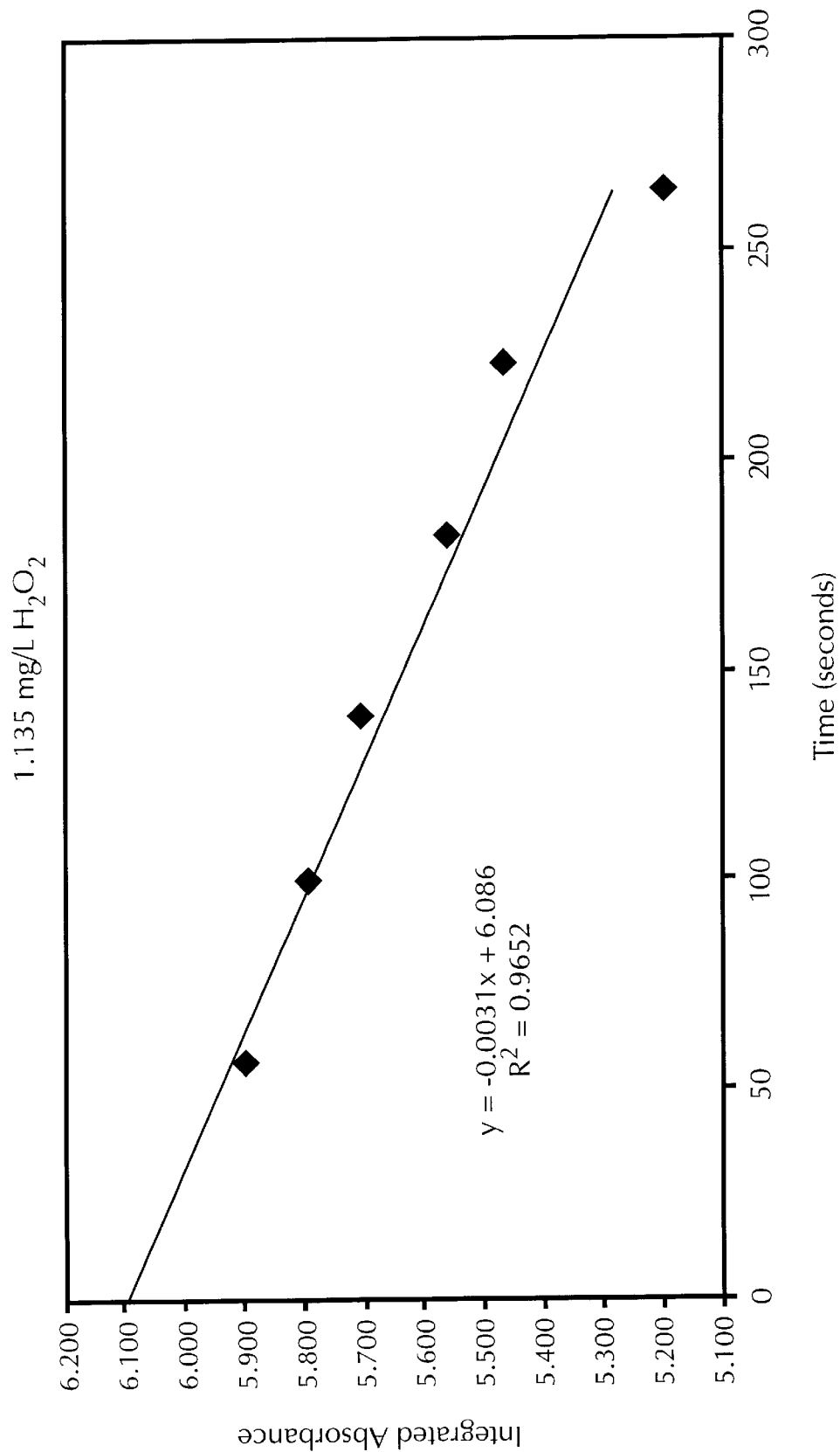
FIG. 1 is a graph of the integrated absorbance of hydrogen peroxide for different times after injection of the hydrogen peroxide into a chamber at an initial concentration of 1.135 milligrams of hydrogen peroxide per liter.

These drawings are provided for illustrative purposes only and should not be used to unduly limit the scope of the invention.

DETAILED DESCRIPTION OF THE INVENTION

Broadly speaking, the methods of this invention are for establishing and/or using a monotonic functional relationship between the concentration of an analyte and the integrated absorbance for a spectral region of interest. Again, broadly speaking, the methods of this invention can be used with any analyte (i) that decomposes during the time experimental spectral data for determining the monotonic functional relationship are being obtained, or (ii) whose spectral data are pressure sensitive at pressures below a given pressure, or (iii) that decomposes during the time the spectral data are being obtained and whose spectral data are pressure sensitive. One such analyte is hydrogen peroxide, which is used in vapor phase sterilization processes and whose concentration must be accurately known.

As used herein, "decompose," "decomposes," "decomposition," and the like should be understood to include or refer to classic chemical decomposition (breakdown) of the analyte to form other species (e.g., the decomposition of hydrogen peroxide to form water and oxygen), addition reactions of the analyte to form other species, and any other chemical or physical transformation of the analyte that results in the analyte no longer being available for measurement. Accordingly, if successive measurements for the presence of an analyte that decomposes are made, the measurements will result in successively smaller values. If the rate of decomposition is so low that successive measurements for the presence of an analyte using the measurement technique of interest do not result in successively smaller values, that analyte with that measurement technique will not be perceived as being an analyte that decomposes although with a sufficiently sensitive measurement technique and/or longer times between sampling, that analyte would be considered to be one that decomposes.

By "spectral data" and the like are meant data resulting from spectrophotometry, regardless of the type of data or instrument and regardless of the portion or portions of the electromagnetic spectrum used. For example, and broadly speaking, when using a Fourier Transform Infrared (FTIR) instrument, the initial data may be in the form of one or more interferograms, which may then be combined and transformed using Fourier mathematics to produce a spectrum from which an integrated absorbance can be calculated.

Various parts of the visible and non-visible spectrum have been used in spectrophotometry, including the ultraviolet (wavelengths of from about 200 nanometers to about 400 nanometers), visible (wavelengths of from about 400 nanometers to about 700 nanometers), near-infrared (wavelengths of from about 700 nanometers to about 2000 nanometers), and infrared (wavelengths of from about 2000 nanometers to about 300,000 nanometers) light regions. As will be understood by one skilled in the art, any region or regions of the spectrum can be used in this invention, depending on the analyte to be measured as well as on what other species are present in the system. For hydrogen peroxide, applicants prefer to use the infrared region, particularly wavenumbers of 1180 $cm^{-1}$ (approximately 8475 nanometers) through 1331 $cm^{-1}$ (approximately 7513 nanometers). That is because between in the region of 1180 $cm^{-1}$ to 1331 $cm^{-1}$, the signal and peak for hydrogen peroxide are strong and those for water are minimal, in other words, there is almost no overlap for those two species within that region. That is advantageous because hydrogen peroxide is often sold in aqueous liquid solutions and hydrogen peroxide vapor (used, for example, for vapor phase sterilization) is typically produced by vaporizing such liquid solutions, thereby producing a gas containing both hydrogen peroxide and water.

As is known by those skilled in the art, when considering electromagnetic radiation to be a wave (as opposed to a particle stream), "wavelength" is the linear distance between two successive amplitude maxima of the radiation beam, "frequency" is the number of oscillations of the wave passing a given point per second, and in a vacuum, wavelength multiplied by frequency yields a constant, namely, the speed of light ($3 \times 10^{10}$ centimeters per second). "Wavenumber" may also be used to describe electromagnetic radiation. It is the number of waves per unit length, in other words, the reciprocal of the wavelength. The unit for wavenumber is usually reciprocal centimeters or $cm^{-1}$.

Spectrophotometry makes use of the Beer-Lambert Law, one formulation of which is that equal thicknesses of a given light-absorbing material will absorb the same fraction of the light energy incident upon them. That is embodied in the equation:

$$P = P_0(10^{-aLC})$$

or light energy per unit time (power) leaving a specimen (indicated as "P") equals the light energy per unit time entering the specimen (indicated as "$P_0$") multiplied by ten to the power "–aLC," where "a" is the absorptivity (or extinction coefficient) of the light-absorbing material, "L" is the path length of the energy through the specimen containing the light-absorbing material, and "C" is the concentration of the light-absorbing material in the specimen. Transmittance is P divided by $P_0$, which equals $10^{-aLC}$.

Absorbance, which is often used to report spectrophotometric results rather than transmittance, is represented by "A" and defined as equal to aLC. Absorptivity (or extinction coefficient) "a" is a property of the light-absorbing material. For a light-absorbing material that follows the Beer-Lambert Law, absorptivity "a" is constant for the material, at least within the concentration range of interest. In a given instrument, the path length "L" through the specimen containing the light-absorbing material is constant. Therefore, for a light-absorbing material that follows the Beer-Lambert Law, absorbance "A" is directly proportional to concentration "C" of the light-absorbing material in the specimen.

As will be appreciated from consideration of the foregoing, it is desirable to choose a portion of the electromagnetic spectrum to detect and determine the concentration of the analyte of interest where there will be no (or no significant) absorption by any other species likely to be present. If another species is present whose absorption is significant, there will need to be some way to back out (i.e., subtract or account for) the absorption attributable to that other species so that the absorption (and therefore the concentration) attributable only to the analyte of interest can be determined. On the other hand, if a portion of the spectrum is used where the analyte of interest absorbs a significant amount of energy but there is no significant absorption by any other species that may be present, the presence of those other species should make no significant difference in the total amount of absorption within that selected portion of the spectrum.

For a species that follows the Beer-Lambert Law, the absorbance attributable to that species should remain unchanged even if other species are present. Therefore, it is most convenient to state the concentration of each such species in units of mass of the species of interest per unit of volume.

It was known that pressure can effect the width of a peak in an absorbance spectrum for an analyte in a gas phase sample. See, e.g., Jeffrey I. Steinfeld, *Molecules And Radiation—An Introduction To Modern Molecular Spectroscopy*, page 229 (The MIT Press 1979): "Finally, in any gas phase sample, there will be a collision broadening whose magnitude in Hz is roughly equal to the gas-kinetic collision frequency Z in the gas. This broadening is roughly of the order of 10 MHz/torr of gas pressure." Thus, at pressures around atmospheric, for a given amount of a first gaseous analyte mixed with a second gas that has no absorbance within the spectral region used for the analyte, even a substantial reduction in pressure, such as by removing all of the second gas but leaving all of the gaseous analyte, would be expected to have minimal effect on the width of the one or more of the analyte's absorbance peaks within that spectral region and minimal effect on detection and accurate determination of the analyte.

This can be seen by assuming that the gaseous analyte provides 1 torr of pressure (1 millimeter of mercury) in the chamber and has a strong peak within the spectral region used and that a second gas that is then added provides 759 torr of pressure in the chamber. According to Steinfeld, above, addition of the second gas to raise the pressure from 1 torr to 760 torr would broaden the peak by approximately 10 MHz/torr multiplied by 759 torr or $7.59 \times 10^9$ Hz (which is equal to $0.0759 \times 10^{11}$ Hz). If we assume that the FTIR spectrophotometric instrument used has a "resolution"

(spectral bandpass) of 4 wavenumbers or 4 cm$^{-1}$ (which when multiplied by the speed of light, $3\times10^{10}$ cm/sec, equals $1.2\times10^{11}$ Hz), it can be seen that the collision broadening due to the 759 torr pressure increase would be expected to have a negligible effect (0.0759 compared to 1.2), in other words, would not be noticeable. Therefore, for that same FTIR instrument, a reduction in pressure from 760 torr to 1 torr would also have negligible effect because the peak would be narrowed by the same amount ($0.0759\times10^{11}$ Hz). (See also Gerhard Herzberg, *Molecular Spectra And Molecular Structure*, II. Infrared And Raman Spectra Of Polyatomic Molecules, page 532 (D. Van Nostrand Company, Inc. 1945), which shows the changes in the shape of the infrared spectra for gaseous HCl with a change in pressure.)

It was also known that broadening of the absorption curve is accompanied by a reduction in the height of the peak; however, it was also thought that the area under the absorption curve, i.e., the integrated absorbance, would remain constant. See, e.g., Douglas A. Skoog et al., *Principles Of Instrumental Analysis*, Fifth Edition, pages 311–312 (Harcourt Brace College Publishers 1998), which discusses the effect of a change in slit width (slit width helps determine resolution for certain types of spectrophotometers): "In both sets of spectra, the areas under the individual peaks are the same, but wide slit widths result in broader lower peaks."

Accordingly, as will be further described below, it was most surprising to applicants to discover that for a constant amount of hydrogen peroxide (the analyte of interest) in the chamber in which the hydrogen peroxide was being measured by the FTIR instrument used, changing the amount of dry air in the chamber and therefore the total pressure would, below a certain pressure, have a significant effect on the absorbance of the hydrogen peroxide. As previously indicated, applicants found that below a pressure of about 230 torr, the integrated absorbance was about 20% lower than it was for the same amount of hydrogen peroxide in the chamber when a sufficient amount of dry air was present to make the total pressure atmospheric (i.e., 760 torr), all else being equal. In other words, the Beer-Lambert Law was violated by a change in the total pressure, even though the partial pressure of the hydrogen peroxide analyte (and its concentration in units of mass per unit volume) remained constant.

Thus, as used herein, the terms "pressure sensitive," "pressure sensitive spectral data," "whose spectral data are pressure sensitive at pressures below a given pressure," and the like refer to this phenomenon, namely, that for a constant amount of analyte (i.e., a constant mass of analyte per unit volume), with all else being equal, the integrated absorption for that analyte changes significantly at some pressure P. For example, for a given spectral region and a given analyte whose spectral data are pressure sensitive, the analyte's integrated absorbance could be constant as the pressure decreases within pressure range $P_1$ to $P_2$, change noticeably but slowly as the pressure decreases in pressure range $P_2$ to $P_3$, change more rapidly as the pressure decreases within pressure range $P_3$ to $P_4$, and even change abruptly at some pressure $P_5$ below pressure $P_4$. It does not matter whether an analyte has more than one such pressure P below which the change in absorbance would cause a significant problem or whether any of those pressures is known exactly or even approximately. All that need be known is that there are one or more pressures P below which the integrated absorption changes enough so that the change(s) is (are) significant with respect to the detection and concentration determinations being made and therefore for which a method of this invention should be used to prevent "erroneous" integrated absorbance values from being used in determining the monotonic functional relationship between concentration and integrated absorbance.

In addition to the pressure sensitivity of its spectral data, hydrogen peroxide decomposes in the vapor phase, thereby posing a challenge in trying to establish a monotonic functional relationship between integrated absorbance and concentration. As explained above, because hydrogen peroxide decomposes, its concentration decreases and the physical property indicative of the concentration (absorption) also decreases. Applicants overcame both of these problems (pressure sensitivity of the spectral data and decomposition) and were able to establish the monotonic functional relationship.

Thus, the methods of this invention can be used for any analyte whose spectral data are pressure sensitive, for any analyte that decomposes, or for any analyte that decomposes and whose spectral data are pressure sensitive. The methods can be used with analytes in any state of matter, although it is likely that the spectral data for liquid and solid analytes will not display pressure sensitivity (at least within the range of normal pressures).

Applicants' work with hydrogen peroxide is instructive and the same procedures they used for establishing the monotonic functional relationship between concentration and integrated absorbance for hydrogen peroxide could be used for any other analyte of interest posing one or both of those challenges (i.e., pressure sensitivity of the spectral data and decomposition).

Samples of aqueous liquid solution of hydrogen peroxide (nominally 30% w/w) were used in the experiments. The hydrogen peroxide solution was obtained from VWR Scientific Products, located in West Chester, Pa. Just before its use, the hydrogen peroxide concentration was determined to be 30.2% w/w using a ceric sulfate titration. The density of the liquid solution was approximately 1.1 grams/cubic centimeter.

Samples were injected into a custom built device having a stainless steel chamber with a volume of 186 liters. Although the device was custom built, the design is not critical and any device can be used in conducting the methods of this invention that allows the required data to be collected. A large chamber (such as one with a volume of 186 liters) has a number of benefits. For example, the ratio of its surface area to its volume is lower than that of a small chamber, and the decomposition of hydrogen peroxide is thought to be hastened by contact with surfaces. A larger chamber has a higher heat capacity as compared to a smaller chamber, thereby reducing variations in the temperature attributable to, for example, variations in ambient temperature and injection of the hydrogen peroxide and thereby facilitating temperature control. All the surfaces the analyte of interest contacts should be as inert as possible with respect to the analyte (e.g., should not promote its decomposition).

The chamber interior was coated with a thin layer of FOMBLIN brand perfluorinated grease obtained from Inland Vacuum Industries, Inc. (Churchville, N.Y.). The purpose of the grease was to render the inner surface of the chamber as inert as possible to reduce the rate of decomposition of the hydrogen peroxide.

The chamber walls were heated with hot air and electricity. Internal (chamber) pressure was measured in two ways, first, with an electronic transducer (pressure transducer type 122A, MKS Instruments, Inc., Andover, Mass.), which operates at pressures up to 100 torr, and second, with an analog gauge (Ametek U.S. Gauge, Sellersville, Pa.). Internal (chamber) temperature was monitored with an analog thermometer (Long Stem Thermometer, Model DF10, Masterbuilt Mfg., Inc., Columbus, Ga.), whose probe extended into the interior of the chamber.

Aliquots of the hydrogen peroxide liquid solution were injected into the chamber with a syringe, the opening of whose needle was forced into the chamber through a resilient seal, much like the stopper-seal on a vial of medicine through which medical personnel can withdraw medicinal solutions with syringes for injection into patients. Vacuum was drawn on the chamber before injection of the hydrogen peroxide aliquots using a vacuum pump (Model RA 0025-E5Z6-1006, Busch, Inc., Virginia Beach, Va.). The pump could reduce the pressure in the chamber to about 2 torr if the pump were run for a sufficient time. The amount of solution injected for the various runs was typically not more than a few milliliters. For example, to obtain a concentration in the chamber of 1.135 milligrams of hydrogen peroxide per liter (1.135 mg/L), approximately 0.64 milliliters (0.7 grams) of the hydrogen peroxide liquid solution were injected. The temperature was, except for the temperature sensitivity runs, only a few degrees above ambient (typically approximately 35° C.). The warmth and low pressure in the chamber caused the small amount of liquid injected to flash into vapor rapidly upon injection. For non-quantitative studies, the aliquots were measured by volume in the syringe. For quantitative studies (i.e., studies in which the number of milligrams of hydrogen peroxide injected into the chamber had to be accurately known), the quantities of hydrogen peroxide solution to be injected were determined as the difference in weight of the syringe before and after the solution to be injected had been expelled from the syringe into the chamber.

Absorbance measurements were taken using a Fourier Transform Infrared (FTIR) spectrophotometer, Model No. TSO-20 marketed by Analect Instruments, Inc., located in Irvine, Calif. The optical path through the chamber was measured to be 18 inches (45.7 centimeters) and was sealed with salt windows, one sodium chloride and one potassium chloride. (The composition of the windows is not critical and any material can be used that allows the required data to be taken.) The bandpass was set at 4 $cm^{-1}$.

After drawing a vacuum on the chamber using the vacuum pump, sixty-four background scans were taken by the Analect FTIR instrument and averaged to obtain a background spectrum. The final value or measurement from the FTIR instrument is the integrated absorbance over the spectral range of interest. For hydrogen peroxide, the spectral region of 1180 $cm^{-1}$ to 1331 $cm^{-1}$ was used. In some cases, water was also determined, using two wavenumber regions, 1590 $cm^{-1}$ to 2030 $cm^{-1}$ and 3095 $cm^{-1}$ to 3912 $cm^{-1}$.

One aspect of the invention concerns establishing a monotonic functional relationship for an analyte that decomposes while the data from which the relationship will be established are being collected. As noted above, hydrogen peroxide begins to decompose immediately upon injection into the chamber but applicants overcame this problem in the following manner.

To obtain the data underlying FIG. 1, a known amount of hydrogen peroxide solution was injected into the chamber, and the hydrogen peroxide vaporized rapidly. Sufficient dry air from a compressed air cylinder at room temperature and 134.7 psia (928 kPa) was rapidly injected into the chamber to bring the pressure in the chamber to approximately atmospheric (raising the pressure to atmospheric required only about 30 seconds and was completed before commencement of the data scans described below). Using the concentration of hydrogen peroxide in the liquid solution, which was precisely known from the above-described analytical technique, the quantity of solution injected, which was carefully determined by weight difference (the weight of the syringe containing hydrogen peroxide solution minus the weight of the emptied syringe), and the volume of the chamber (186 liters), the initial vapor phase concentration of hydrogen peroxide was calculated in units of milligrams of hydrogen peroxide per liter. For the data upon which FIG. 1 is based, the initial concentration of hydrogen peroxide was 1.135 milligram of hydrogen peroxide per liter.

A timer was started at the time of injection. Sixteen sample scans were taken for each data point. An interferogram resulted from each scan. The sixteen scans were combined and the required mathematical operations (Fourier transformation) were performed on the combination, thereby generating a single absorbance spectrum within the spectral region of interest for the analyte (1180 $cm^{-1}$ to 1331 $cm^{-1}$ for the hydrogen peroxide), and the integrated absorbance was calculated from that spectrum.

With reference to the first (left-most) data point, the integrated absorbance was calculated to be approximately 5.9. The sixteen FTIR instrument scans from which the integrated absorbance for each data point was calculated required a total of approximately 30 seconds to perform. For that first data point, the first scan of the set of sixteen scans started a little over 35 seconds after injection and the set of scans ended a little over 65 seconds after injection. The time for the single integrated absorbance value resulting from that set of scans was taken at the mid-point or slightly over 50 seconds.

The integrated absorbance for this set of scans (approximately 5.9) was plotted against the time mid-point of slightly over 50 seconds for the first data point. A second set of sixteen scans was started about 85 seconds after injection (about 20 seconds after the last scan of the first set) and ended about 115 seconds after injection. The integrated absorbance for the hydrogen peroxide for this second set of scans was calculated to be slightly under 5.8 and that value was plotted against the time mid-point of 100 seconds to give the second point on the graph of FIG. 1. Four more successive points were determined in the same manner and are also plotted on the graph.

Using regression analysis and assuming that a straight line would fit the data over the time period shown, the respective concentration and absorbance data were associated by fitting them ($R^2$=0.9652) to the line y=−0.0031x+6.086 (y being the integrated absorbance and x being the elapsed time since the time of hydrogen peroxide injection). The y intercept value of 6.086 indicates that at time $t_0$ (the moment before decomposition began), the integrated absorbance was 6.086. In other words, if at the moment just before decomposition began the integrated absorption of the hydrogen peroxide for a concentration of 1.135 milligrams per liter could have been instantaneously determined, the value determined would have been 6.086.

In similar fashion, different known amounts of liquid hydrogen peroxide solution were injected, a set of FTIR scans was run for each selected time following injection, the integrated absorbance was determined for each such time, and the time $t_0$ integrated absorbance value was determined by fitting the data for each known initial vapor-phase hydrogen peroxide concentration and, in essence, extrapolating back to time zero (the moment just before decomposition began). As will be described below, applicants used these time $t_0$ absorbance values to obtain the monotonic functional relationship between the concentration of the vapor phase hydrogen peroxide analyte at the moment just before decomposition commenced and the integrated absorbance.

As used herein, the terms "extrapolating from the integrated absorbance for the first time and the one or more subsequent times to the time at which the decomposition of the analyte commences to thereby establish at a time before the decomposition commences an estimated integrated absorbance . . . ," "extrapolating back to time zero," "extrapolated," and the like refer to any technique (whether graphical, analytical, or otherwise) by which the integrated absorbance values for times subsequent to commencement of the decomposition of the analyte of interest are used to determine (or estimate) the integrated absorbance value at a moment just before decomposition begins. Such extrapolation will often be done analytically by fitting a curve to the data and determining the intercept of the curve at time zero ($t_0$); however, the data could also be plotted on a graph, a curve drawn on the graph that appears to be appropriate, and the intercept read from the graph. Preferably, the extrapolation is done analytically.

The data upon which the graph of FIG. 1 is based were obtained at a chamber pressure of approximately atmospheric pressure because dry air was added; however, when earlier runs were performed, dry air was not being added because applicants had not realized that the hydrogen peroxide spectral data were pressure sensitive and had not discovered how to overcome that problem. Without the addition of the dry air, the pressure in the chamber would be the pressure resulting from flashing of the small hydrogen peroxide liquid aliquots in the chamber plus the few torr of pressure resulting from the air in the chamber that the vacuum pump could not remove. After they realized there was a problem and how it might be corrected, applicants performed pressure sensitivity studies.

For these studies, the vacuum pump was run until the pressure was 2 torr (about 0.3 kPa) in the chamber, and a background spectrum was obtained. A constant volume (e.g., 0.5 milliliters) of the above-described aqueous hydrogen peroxide liquid solution of known concentration was injected at the beginning of each pressure level run. The hydrogen peroxide liquid solution rapidly flashed into vapor, and the total pressure for each pressure level run was adjusted to a different total pressure level by rapidly adding a different amount of the 134.7 psia (928 kPa) dry air after injection of the hydrogen peroxide liquid solution. Addition of the air was completed in less than roughly 30 seconds and before any of the absorbance scans at that pressure level commenced. For each pressure level, and using the method described above in connection with FIG. 1 for correcting for the hydrogen peroxide decomposition, consecutive sets of Analect FTIR scans at different times after injection of the hydrogen peroxide liquid solution were made and the integrated absorbance for the hydrogen peroxide at time $t_0$ (the time just after flashing and just before decomposition began) was determined for each total pressure for that constant amount of hydrogen peroxide. The spectral region used for the hydrogen peroxide was the same as before, namely, 1180 $cm^{-1}$ to 1331 $cm^{-1}$.

Figure 2:
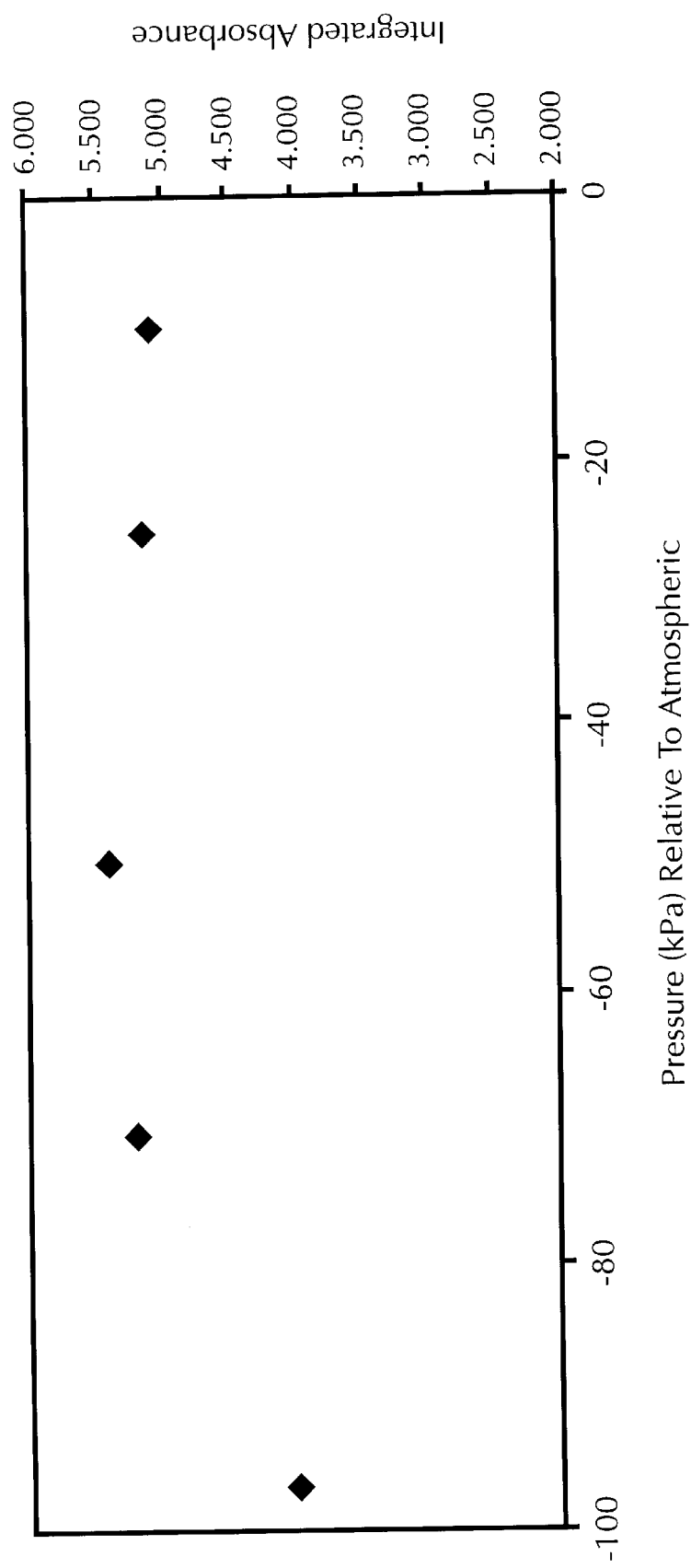
FIG. 2 is a graph of the integrated absorbance of a constant initial concentration of hydrogen peroxide in the chamber for different total pressures in the chamber.

FIG. 2 shows the results of the pressure study for the injection of 0.5 milliliters of hydrogen peroxide liquid solution. Injection of that amount of hydrogen peroxide liquid solution into the "empty" chamber (which had been evacuated by the vacuum pump down to a pressure of 2 torr, that pressure resulting from the small amount of air remaining the chamber) and its flashing into vapor would add roughly 3 torr of pressure, to give a total pressure in the chamber of about 5 torr. Because an atmosphere of pressure is 760 torr or 101.3 kPa (kiloPascals), a perfect vacuum would have a pressure of 760 torr below atmospheric or 101.3 kPa below atmospheric. The first (left-most) data point in FIG. 2 shows the regressed (i.e., from curve fitting) time $t_0$ integrated absorbance at a pressure of about 97 kPa below atmospheric or about 30 torr absolute or 30 torr above zero pressure (zero being a perfect vacuum). The other data points show time $t_0$ integrated absorbance values for pressures of roughly 70 kPa below atmospheric (about 230 torr absolute), roughly 50 kPa below atmospheric (about 380 torr absolute), roughly kPa below atmospheric (about 570 torr absolute), and roughly 10 kPa below atmospheric (about 680 torr absolute).

Moving from the right side of the graph of FIG. 2 towards the left side, the integrated absorbance values as the total pressure continues to decrease below atmospheric pressure remains roughly constant at a value of about 5 until after the total pressure decreases below about 230 torr absolute. Thus, when the pressure is about 30 torr absolute, the integrated absorbance is only about 4. That means that although the initial concentration of hydrogen peroxide in units of mass of hydrogen peroxide per unit volume remains constant (because the same amount of hydrogen peroxide liquid solution is injected at the beginning of each run), and although one would therefore expect the integrated absorbance to remain constant regardless of the amount of dry air added to the chamber (the dry air does not react with the hydrogen peroxide or itself absorb in the spectral region used), applicants found that in fact the integrated absorbance fell by about 20% (from about 5 to about 4) at some point when the total pressure was below 230 torr.

Applicants do not know the exact pressure P at which this pressure sensitivity of the hydrogen peroxide spectral data becomes significant; however, they do know that at some pressure below approximately 230 torr, the pressure sensitivity is significant (in other words, cannot be ignored). Accordingly, applicants know that data used for establishing the monotonic functional relationship between concentration and absorbance should all be collected at pressures sufficiently similar so that either none of the data is being significantly affected by the pressure sensitivity phenomenon or all are being affected to an equal degree. Because without additional work, and perhaps a substantial amount of work (i.e., pressure studies), it may be difficult to determine whether all of the data are being affected to an equal degree, in the first instance, it would seem to be easier and safer to use total pressures at least approximately equal to each other and sufficiently above pressure P to reduce or eliminate the effect of pressure sensitivity. Thus, for example, for hydrogen peroxide, if all the data for establishing the monotonic functional relationship are collected at approximately atmospheric pressure, the results of the pressure studies (e.g., shown in FIG. 2) indicate that any effect of total pressure on the spectral data for hydrogen peroxide will be insignificant. Again, it should be understood that as used herein, the terms "pressure P having been previously determined," "determining pressure P," and the like do not require that pressure P be determined (or known) exactly or even approximately; those terms refer only to knowledge of the fact that there are one or more pressures P below which the integrated absorption changes enough so that the change (s) is (are) significant with respect to the detection and concentration determinations being made (and therefore for which a method of this invention should be used to prevent "erroneous" integrated absorbance values from being used in determining the monotonic functional relationship between concentration and integrated absorbance).

To overcome the effect of pressure sensitivity, dry air was rapidly injected. Dry air was used because it is essentially "inert" to the hydrogen peroxide and because air will often be present in the apparatus for other reasons. In other words, it does not react chemically with the hydrogen peroxide, the components of the dry air (nitrogen, oxygen, and trace gases, e.g., argon) do not have any significant absorbance within the spectral region of interest used for the hydrogen peroxide (1180 $cm^{-1}$ to 1331 $cm^{-1}$), and it does not otherwise adversely affect the data collection or results.

It will be apparent to one skilled in the art that any substance could be used to increase the total pressure for an analyte whose spectral data are pressure sensitive provided the substance is at least substantially if not almost completely inert to the analyte of interest. The general requirements for such an additional substance include that it not react to any significant degree (and preferably not at all) with the analyte of interest and that it not absorb light energy to any significant degree (and preferably not at all) within the spectral region used for the analyte of interest. (As used in the claims, "inert" should be understood to include "essentially inert" and "substantially inert"—being 100% inert is not required.) Preferably, the additional substance should also be in a form so that it can be added rapidly to the chamber in which the spectral data will be taken so that its addition is completed before any spectral data are taken. Thus, if the monotonic functional relationship is to be established for an analyte in the gas phase, the additional substance used to raise the pressure above that at which the spectral data are pressure sensitive (pressure P) is preferably another gas. Air has a number of advantages as the additional substance, since some of it will usually be in the chamber even before the analyte of interest is injected, it is obviously readily available, and it is almost free; however, depending on the analyte's sensitivity to water, the air may have to be dried. If the analyte of interest is sensitive to oxygen, air probably could not be used as the substance to increase the pressure above pressure P.

The effect of temperature on the spectral data was also investigated. The same spectral band (1180 $cm^{-1}$ to about 1331 $cm^{-1}$) was again used for the hydrogen peroxide. A background spectrum was obtained for a pressure of 20 kPa below atmospheric (an absolute pressure of about 610 torr) at each temperature level of the study. A constant volume of 0.5 milliliters of the above-described aqueous hydrogen peroxide liquid solution of known concentration was injected into the chamber, which was under the vacuum drawn by the vacuum pump, and the solution rapidly flashed into vapor. The pressure was rapidly brought up to 20 kPa below atmospheric (an absolute pressure of about 610 torr) by injecting a sufficient amount of the 134.7 psia (928 kPa) dry air into the chamber. The target pressure was reached within no more than 30 seconds and in any case, before the Analect FTIR instrument spectral scans commenced. For each temperature level, and using the method described above, several sets of spectral scans were made at different times after injection of the hydrogen peroxide liquid solution and for each set the time $t_0$ integrated absorbance was determined.

Figure 3:
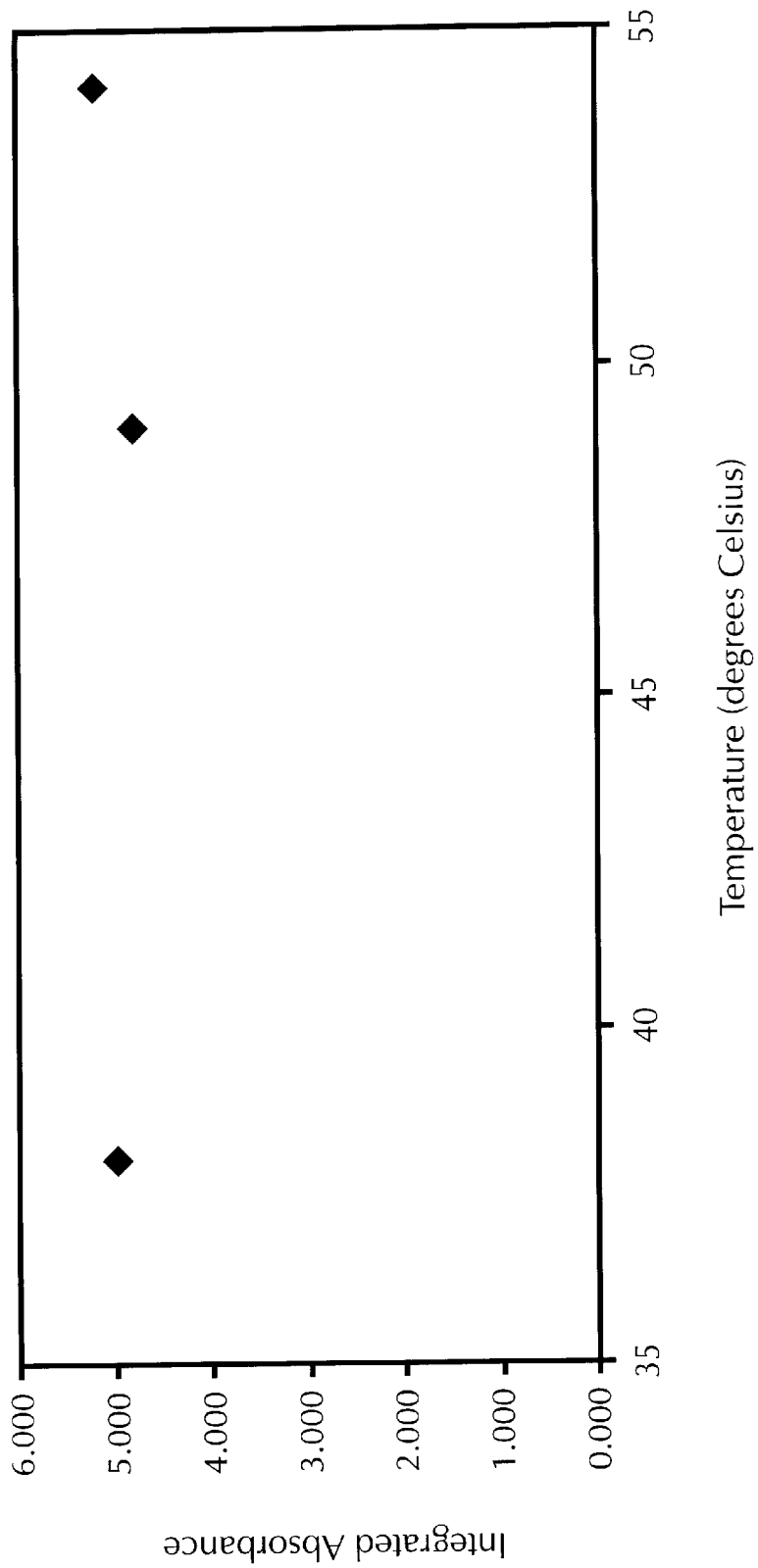
FIG. 3 is a graph of the integrated absorbance of a constant initial concentration of hydrogen peroxide in the chamber for different temperatures in the chamber.

FIG. 3 shows that the time $t_0$ integrated absorbance was approximately 5.0 for each of the three temperature levels studied (namely, about 38° C., 49° C., and 54° C.). Thus, at least across this temperature range, the spectral data for hydrogen peroxide do not display temperature sensitivity even though they are pressure sensitive. Other analytes for which one or more of the methods of this invention are used to establish a monotonic functional relationship between concentration and integrated absorbance may in fact display such temperature sensitivity. If the analyte of interest were temperature sensitive, the data would be collected within a temperature range in which any such temperature sensitivity did not significantly affect the spectral data.

Armed with the knowledge that the spectral data for hydrogen peroxide are pressure sensitive but not temperature sensitive within the pressure and temperature ranges of interest, spectral data were collected using the procedures described above on three separate days at a total chamber contents pressure of 20 kPa below atmospheric (an absolute pressure of about 610 torr) and a chamber contents temperature of about 48° C. The data from the three days were found to be consistent and were used together in one large data set to establish the monotonic functional relationship between concentration and absorbance for hydrogen peroxide.

The result of the data collection, Fourier transformation, etc. was that applicants had a final data set consisting of initial (time $t_0$) hydrogen peroxide vapor phase concentrations and the respective time $t_0$ integrated absorbances (one integrated absorbance value for each concentration). Those data were then curve fit and the resulting line had the equation y=4.7382x+0.4263, where y is the integrated absorbance at initial time $t_0$ (the time immediately after injection of the known amount of hydrogen peroxide and immediately before hydrogen peroxide decomposition commences) and x is the calculated vapor phase hydrogen peroxide concentration at time $t_0$ in milligrams of hydrogen peroxide per liter. The fit was excellent (0.996 coefficient of correlation, 0.992 coefficient of determination, and 6.7% relative standard error of regression). The data points and the plot of the line are shown in the graph in FIG. 4. The data point at an x value (calculated initial hydrogen peroxide vapor phase concentration) of 1.135 milligrams per liter has a y value (integrated absorbance) of 6.086, which values are consistent with the data determined for FIG. 1 (see discussion of FIG. 1, above). The equation for this line (y=4.7382x+0.4263) is a representation or a determination of the monotonic functional relationship between (A) the integrated absorbance of spectral energy within a spectral region of interest of an analyte that decomposes during the time experimental spectral data for determining the relationship are being obtained and whose spectral data are pressure sensitive below a total pressure P (i.e., the hydrogen peroxide) and (B) the concentration of the analyte (i.e., hydrogen peroxide) before decomposition commences.

The terms (a) "associating each of the known initial concentrations with its respective estimated integrated absorbance of spectral energy within the spectral region of interest to thereby determine for the analyte at a total pressure not less than pressure P the monotonic functional relationship between the concentration before the decomposition commences and the integrated absorbance of spectral energy within the spectral region of interest of the analyte," (b) "associating each of the known initial concentrations with its respective estimated integrated absorbance of spectral energy within the spectral region of interest to thereby determine for the analyte the monotonic functional relationship between the concentration before the decomposition commences and the integrated absorbance of spectral energy within the spectral region of interest of the analyte," (c) "associating each of the known a initial concentrations with its respective integrated absorbance of spectral energy within the spectral region of interest to thereby determine for the analyte at a total pressure not less than pressure P the monotonic functional relationship between the concentration and the integrated absorbance of spectral energy within the spectral region of interest of the analyte," and (d) the like each refer to pairing the concentration with its respective absorbance and using the pairing to establish the monotonic functional relationship. Such "pairing" and "establishing" may be accomplished in any suitable manner. The "pairing" and "establishing" may be nothing more than having a simple look-up table in which each known concentration is paired with the absorbance previously determined for it. Preferably the absorbance and concentration data will be paired and the monotonic functional relationship will be determined by analytically fitting a curve to the paired data using regression analysis.

Figure 4:
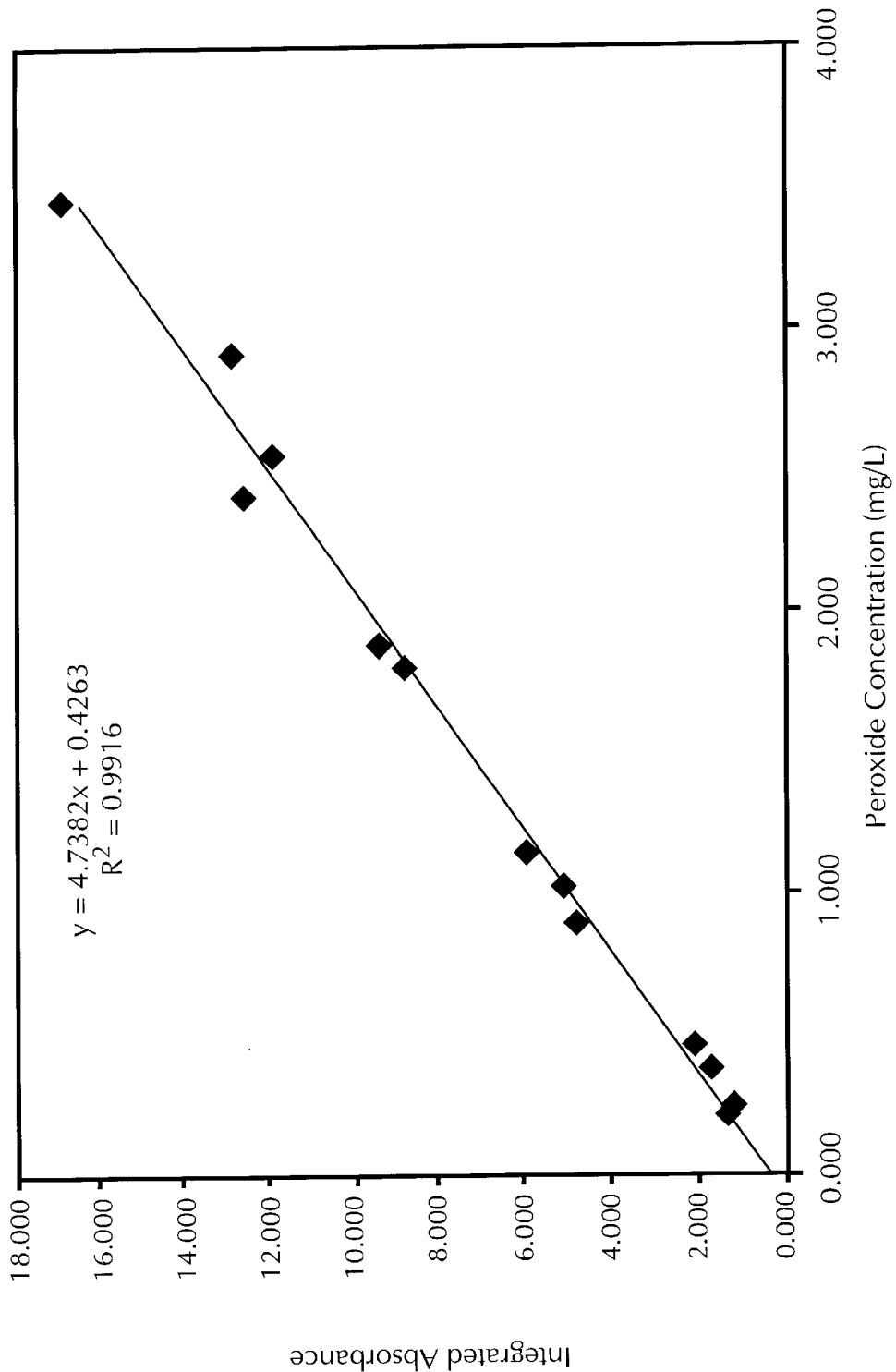
FIG. 4 is a graph of a monotonic functional relationship between concentration and integrated absorbance that was established through a method of this invention and that was used to determine the regressed concentration values displayed in the table of FIG. 5.

The graph of FIG. 4 or the equation of the curve shown in that graph can be used to determine hydrogen peroxide concentration from integrated absorbance values determined for the same spectral region used to obtain the curve, with the same path length, etc. A change in path length could easily be corrected for using the fact that, as discussed above, absorption is directly proportional to path length and is directly proportional to concentration. The monotonic functional relationship once established for an analyte determined using a method of this invention can be used to calibrate the same instrument or other instruments, making appropriate corrections for any changes in path length etc.

The table of FIG. 5 shows in the first two columns the thirteen pairs of x-y values used for the thirteen data points in FIG. 4 (the two left-most data points overlap in FIG. 4 because, as can be seen from the first two rows of the table of FIG. 5, the concentration and integrated absorbance values are so close). The first column of the table indicates the "prepared concentration," i.e., the initial concentration of the hydrogen peroxide in the vapor phase (calculated based on a known amount of hydrogen peroxide solution being injected into the chamber and the solution's known concentration of hydrogen peroxide), which is at time $t_0$ (i.e., the time immediately after injection and immediately before the injected liquid hydrogen peroxide and water flash into the vapor phase). The second column shows for each prepared (initial) concentration value the extrapolated integrated absorbance value at that time $t_0$, extrapolated from the experimental spectral data (as for FIG. 1). The third column indicates the calculated time $t_0$ hydrogen peroxide concentration based on the absorbance in the second column and using the concentration-absorbance monotonic functional relationship determined as described in connection with FIG. 4. The fourth column shows the percent error between the time to actual concentration (column 1) and the time $t_0$ concentration calculated (predicted) using the monotonic functional relationship for a given measured absorbance (column 3). The percent error is calculated as the column 3 value minus the column 1 value divided by the column 1 value. Thus, for the first row of data, the percent error is 0.211 minus 0.206 divided by 0.206, or 0.005 divided by 0.206, which equals 2.4% (the difference between that value and the value of 2.2% shown in FIG. 5 is due to rounding of the other values in the table).

As will be appreciated by one skilled in the art, the methods illustrated for obtaining and using the monotonic functional relationship between absorbance and concentration for hydrogen peroxide can be used with any analyte (i) that decomposes during the time experimental spectral data for determining the relationship are being obtained, or (ii) whose spectral data are pressure sensitive at pressures below a given pressure, or (iii) that decomposes during the time the spectral data are being obtained and whose spectral data are pressure sensitive.

Variations and modifications will be apparent to those skilled in the art and the following claims are intended to cover all variations and modifications falling within the true spirit and scope of the invention.

We claim:

1. A method for determining the monotonic functional relationship between (A) the integrated absorbance of spectral energy within a spectral region of interest of an analyte that decomposes during the time experimental spectral data for determining the relationship are being obtained and whose spectral data are pressure sensitive below a total pressure P and (B) the concentration of the analyte before decomposition commences, the method comprising the steps:

(a) for a first known initial concentration of the analyte and while intentionally maintaining the total pressure at a pressure not less than pressure P because of the spectral data being pressure sensitive below pressure P: (i) determining the integrated absorbance of spectral energy within the spectral region of interest at a first time after the commencement of the obtention of spectral data, (ii) determining the integrated absorbance of spectral energy within the spectral region of interest at one or more times subsequent to the first time and different from each other if more than one subsequent time is used, and (iii) extrapolating from the integrated absorbance for the first time and the one or more subsequent times to the time at which the decomposition of the analyte commences to thereby establish at a time before the decomposition commences an estimated integrated absorbance of spectral energy within the spectral region of interest for the first known initial concentration;

(b) for each of one or more additional known initial concentrations of the analyte different from the first known concentration and different from each other if more than one additional initial concentration is used and while intentionally maintaining the total pressure at a pressure not less than pressure P because of the spectral data being pressure sensitive below pressure P: (i) determining the integrated absorbance of spectral energy within the spectral region of interest at a first time after the commencement of the obtention of spectral data, (ii) determining the integrated absorbance of spectral energy within the spectral region of interest at one or more times subsequent to the first time and different from each other if more than one subsequent time is used, and (iii) extrapolating from the integrated absorbance for the first time and the one or more subsequent times to the time at which the decomposition of the analyte commences to thereby establish at a time before the decomposition commences an estimated integrated absorbance of spectral energy within the spectral region of interest for each of the one or more additional known initial concentrations; and (c) associating each of the known initial concentrations with its respective estimated integrated absorbance of spectral energy within the spectral region of interest to thereby determine for the analyte at a total pressure not less than pressure P the monotonic functional relationship between the concentration before the decomposition commences and the integrated absorbance of spectral energy within the spectral region of interest of the analyte.

2. The method of claim 1 further comprising determining pressure P prior to carrying out steps (a), (b), and (c).

3. The method of claim 1 further comprising maintaining the total pressure in each of steps (a) and (b) at a total pressure not less than pressure P by adding to the analyte as needed to raise the pressure a gas that is inert to the analyte.

4. The method of claim 3 wherein the gas that is inert to the analyte is dry air.

5. The method of claim 1 wherein the analyte is a sterilant.

6. The method of claim 1 wherein the analyte is a volatile inorganic or organic peroxidant.

7. The method of claim 6 wherein the analyte is hydrogen peroxide.

8. The method of claim 1 wherein the spectral region of interest is the infrared region.

9. The method of claim 8 wherein the spectral region of interest is from about 1180 $cm^{-1}$ to about 1331 $cm^{-1}$.

10. A method for determining in an unknown the concentration of an analyte that decomposes and whose spectral data are pressure sensitive below a total pressure P, the method comprising the steps: (d) while intentionally maintaining the total pressure at a pressure not less than pressure P because of the spectral data being pressure sensitive below pressure P, carrying out the method of claim 1 to determine the monotonic functional relationship for the analyte, (e) while intentionally maintaining the total pressure at a pressure not less than pressure P because of the spectral data being pressure sensitive below pressure P, determining the integrated absorbance for the unknown within the spectral region of interest, and (f) from the monotonic functional relationship determined in step (d) and the integrated absorbance determined in step (e), determining the concentration of the analyte in the unknown.

11. The method of claim 10 wherein the analyte is a sterilant.

12. The method of claim 10 wherein the analyte is a volatile inorganic or organic peroxidant.

13. The method of claim 10 wherein the analyte is hydrogen peroxide.

14. The method of claim 10 wherein the spectral region of interest is the infrared region.

15. The method of claim 14 wherein the spectral region of interest is from about 1180 cm, to about 1331 $cm^{-1}$.

16. A method for determining in an unknown the concentration of an analyte that decomposes and whose spectral data are pressure sensitive below a total pressure P, a monotonic functional relationship between the concentration of the analyte and integrated absorbance at a total pressure not less than pressure P having been previously established using the method of claim 1, the method comprising the steps: (a) while intentionally maintaining the total pressure at a pressure not less than pressure P because of the spectral data being pressure sensitive below pressure P, determining the integrated absorbance for the unknown within the spectral region of interest and (b) from the monotonic functional relationship previously determined at a total pressure not less than pressure P using the method of claim 1, and the integrated absorbance determined in step (a), determining the concentration of the analyte in the unknown.

17. The method of claim 16 wherein the analyte is a sterilant.

18. The method of claim 16 wherein the analyte is a volatile inorganic or organic peroxidant.

19. The method of claim 16 wherein the analyte is hydrogen peroxide.

20. The method of claim 16 wherein the spectral region of interest is the infrared region.

21. The method of claim 20 wherein the spectral region of interest is from about 1180 $cm^{-1}$ to about 1331 $cm^{-1}$.

22. A method for determining the monotonic functional relationship between (A) the integrated absorbance of spectral energy within a spectral region of interest of an analyte that is a peracid or a peroxide and that decomposes during the time experimental spectral data for determining the relationship are being obtained and (B) the concentration of the analyte before decomposition commences, the method comprising the steps:

(a) for a first known initial concentration of the analyte: (i) determining the integrated absorbance of spectral energy within the spectral region of interest at a first time after the commencement of the obtention of spectral data, (ii) determining the integrated absorbance of spectral energy within the spectral region of interest at one or more times subsequent to the first time and different from each other if more than one subsequent time is used, and (iii) extrapolating from the integrated absorbance for the first time and the one or more subsequent times to the time at which the decomposition of the analyte commences to thereby establish at a time before the decomposition commences an estimated integrated absorbance of spectral energy within the spectral region of interest for the first known initial concentration;

(b) for each of one or more additional known initial concentrations of the analyte different from the first known concentration and different from each other if more than one additional initial concentration is used: (i) determining the integrated absorbance of spectral energy within the spectral region of interest at a first time after the commencement of the obtention of spectral data, (ii) determining the integrated absorbance of spectral energy within the spectral region of interest at one or more times subsequent to the first time and different from each other if more than one subsequent time is used, and (iii) extrapolating from the integrated absorbance for the first time and the one or more subsequent times to the time at which the decomposition of the analyte commences to thereby establish at a time before the decomposition commences an estimated integrated absorbance of spectral energy within the spectral region of interest for each of the one or more additional known initial concentrations; and (c) associating each of the known initial concentrations with its respective estimated integrated absorbance of spectral energy within the spectral region of interest to thereby determine for the analyte the monotonic functional relationship between the concentration before the decomposition commences and the integrated absorbance of spectral energy within the spectral region of interest of the analyte.

23. The method of claim 22 wherein the analyte is a sterilant.

24. The method of claim 22 wherein the analyte is a peroxide.

25. The method of claim 22 wherein the analyte is hydrogen peroxide.

26. The method of claim 22 wherein the spectral region of interest is the infrared region.

27. The method of claim 26 wherein the spectral region of interest is from about 1180 $cm^{-1}$ to about 1331 $cm^{-1}$.

28. The method of claim 22 wherein the monotonic functional relationship is established for the analyte in the gas phase.

29. The method of claim 28 wherein the analyte is a sterilant.

30. The method of claim 28 wherein the analyte is a volatile peroxide.

31. The method of claim 28 wherein the analyte is hydrogen peroxide.

32. The method of claim 28 wherein the spectral region of interest is the infrared region.

33. The method of claim 32 wherein the spectral region of interest is from about 1180 $cm^{-1}$ to about 1331 $cm^{-1}$.

34. A method for determining in an unknown the concentration of an analyte that is a peracid or a peroxide and that decomposes, the method comprising the steps: (d) carrying out the method of claim 22 to determine the monotonic functional relationship for the analyte, (e) determining the integrated absorbance for the unknown within the spectral region of interest, and (f) from the monotonic functional relationship determined in step (d) and the integrated absorbance determined in step (e), determining the concentration of the analyte in the unknown.

35. The method of claim 34 wherein the analyte is a sterilant.

36. The method of claim 34 wherein the analyte is a peroxide.

37. The method of claim 34 wherein the analyte is hydrogen peroxide.

38. The method of claim 34 wherein the spectral region of interest is the infrared region.

39. The method of claim 38 wherein the spectral region of interest is from about 1180 $cm^{-1}$ to about 1331 $cm^{-1}$.

40. The method of claim 34 wherein the monotonic functional relationship is established for the analyte in the gas phase.

41. The method of claim 40 wherein the analyte is a sterilant.

42. The method of claim 40 wherein the analyte is a volatile peroxide.

43. The method of claim 40 wherein the analyte is hydrogen peroxide.

44. The method of claim 40 wherein the spectral region of interest is the infrared region.

45. The method of claim 44 wherein the spectral region of interest is from about 1180 $cm^{-1}$ to about 1331 $cm^{-1}$.

46. A method for determining in an unknown the concentration of an analyte that is a peracid or a peroxide and that decomposes, a monotonic functional relationship between the concentration of the analyte and integrated absorbance having been previously established using the method of claim 22, the method comprising the steps: (a) determining the integrated absorbance for the unknown within the spectral region of interest and (b) from the monotonic functional relationship previously determined using the method of claim 22 and the integrated absorbance determined in step (a), determining the concentration of the analyte in the unknown.

47. The method of claim 46 wherein the analyte is a sterilant.

48. The method of claim 46 wherein the analyte is a peroxide.

49. The method of claim 46 wherein the analyte is hydrogen peroxide.

50. The method of claim 46 wherein the spectral region of interest is the infrared region.

51. The method of claim 50 wherein the spectral region of interest is from about 1180 $cm^{-1}$ to about 1331 $cm^{-1}$.

52. The method of claim 46 wherein the monotonic functional relationship was established for the analyte in the gas phase.

53. The method of claim 52 wherein the analyte is a sterilant.

54. The method of claim 52 wherein the analyte is a volatile peroxide.

55. The method of claim 52 wherein the analyte is hydrogen peroxide.

56. The method of claim 52 wherein the spectral region of interest is the infrared region.

57. The method of claim 56 wherein the spectral region of interest is from about 1180 $cm^{-1}$ to about 1331 $cm^{-1}$.

58. A method for determining the monotonic functional relationship between (A) the integrated absorbance of spectral energy within a spectral region of interest of an analyte in the gas phase whose spectral data are pressure sensitive below total pressure P and (B) the concentration of the analyte, the method comprising the steps:

(a) for a first known initial concentration of the analyte and while intentionally maintaining the total pressure at a pressure not less than pressure P because of the spectral data being pressure sensitive below pressure P, determining the integrated absorbance of spectral energy within the spectral region of interest for the first known initial concentration;

(b) for each of one or more additional known initial concentrations of the analyte different from the first known concentration and different from each other if more than one additional initial concentration is used and while intentionally maintaining the total pressure at a pressure not less than pressure P because of the spectral data being pressure sensitive below pressure P, determining the integrated absorbance of spectral energy within the spectral region of interest for each of the one or more additional known initial concentrations; and (c) associating each of the known initial concentrations with its respective integrated absorbance of spectral energy within the spectral region of interest to thereby determine for the analyte at a total pressure not less than pressure P the monotonic functional relationship between the concentration and the integrated absorbance of spectral energy within the spectral region of interest of the analyte.

59. The method of claim 58 further comprising determining pressure P prior to carrying out steps (a), (b), and (c).

60. The method of claim 58 further comprising maintaining the total pressure in each of steps (a) and (b) at a total pressure not less than pressure P by adding to the analyte as needed to raise the pressure a gas that is inert to the analyte.

61. The method of claim 60 wherein the gas that is inert to the analyte is dry air.

62. The method of claim 58 wherein the analyte is a sterilant.

63. The method of claim 58 wherein the analyte is an inorganic or organic peroxidant.

64. The method of claim 58 wherein the analyte is hydrogen peroxide.

65. The method of claim 58 wherein the spectral region of interest is the infrared region.

66. The method of claim 65 wherein the spectral region of interest is from about 1180 $cm^{-1}$ to about 1331 $cm^{-1}$.

67. A method for determining in a gas phase unknown the concentration of an analyte whose spectral data are pressure sensitive below a total pressure P, the method comprising the steps: (d) while intentionally maintaining the total pressure at a pressure not less than pressure P because of the spectral data being pressure sensitive below pressure P, carrying out the method of claim 58 to determine the monotonic functional relationship for the analyte, (e) while intentionally maintaining the total pressure at a pressure not less than pressure P because of the spectral data being pressure sensitive below pressure P, determining the integrated absorbance for the unknown within the spectral region of interest, and (f) from the monotonic functional relationship determined in step (d) and the integrated absorbance determined in step (e), determining the concentration of the analyte in the unknown.

68. The method of claim 67 further comprising maintaining the total pressure in each of steps (d) and (e) at a total pressure not less than pressure P by adding to the analyte as needed to raise the pressure a gas that is inert to the analyte.

69. The method of claim 68 wherein the gas that is inert to the analyte is dry air.

70. The method of claim 67 wherein the analyte is a sterilant.

71. The method of claim 67 wherein the analyte is an inorganic or organic peroxidant.

72. The method of claim 67 wherein the analyte is hydrogen peroxide.

73. The method of claim 67 wherein the spectral region of interest is the infrared region.

74. The method of claim 73 wherein the spectral region of interest is from about 1180 $cm^{-1}$ to about 1331 $cm^{-1}$.

75. A method for determining in an unknown the concentration of an analyte whose spectral data are pressure sensitive below a total pressure P, a monotonic functional relationship between the concentration of the analyte and integrated absorbance having been previously established using the method of claim 58, the method comprising the steps: (a) while intentionally maintaining the total pressure at a pressure not less than pressure P because of the spectral data being pressure sensitive below pressure P, determining the integrated absorbance for the unknown within the spectral region of interest and (b) from the monotonic functional relationship previously determined using the method of claim 58 and the integrated absorbance determined in step (a), determining the concentration of the analyte in the unknown.

76. The method of claim 75 further comprising maintaining the total pressure in step (a) at a total pressure not less than pressure P by adding to the analyte as needed to raise the pressure a gas that is inert to the analyte.

77. The method of claim 76 wherein the gas that is inert to the analyte is dry air.

78. The method of claim 75 wherein the analyte is a sterilant.

79. The method of claim 75 wherein the analyte is an inorganic or organic peroxidant.

80. The method of claim 75 wherein the analyte is hydrogen peroxide.

81. The method of claim 75 wherein the spectral region of interest is the infrared region.

82. The method of claim 81 wherein the spectral region of interest is from about 1180 $cm^{-1}$ to about 1331 $cm^{-1}$.

* * * * *

UNITED STATES PATENT AND TRADEMARK OFFICE
CERTIFICATE OF CORRECTION

PATENT NO.     : 6,794,649 B2
DATED          : September 21, 2004
INVENTOR(S)    : Robert J. Thrash et al.

It is certified that error appears in the above-identified patent and that said Letters Patent is hereby corrected as shown below:

Column 8,
Line 22, change "to" to -- $t_o$ --.

Column 16,
Line 13, insert -- 25 -- between "roughly" and "kPa".

Column 21,
Line 40, change "about 1180 cm," to -- about 1180 $cm^{-1}$ --.

Signed and Sealed this

Twenty-third Day of November, 2004

JON W. DUDAS
*Director of the United States Patent and Trademark Office*